United States Patent
Avdagic et al.

(10) Patent No.: US 7,868,174 B2
(45) Date of Patent: Jan. 11, 2011

(54) FORM OF A BENZENESULFONAMIDE DERIVATIVE

(75) Inventors: Amir Avdagic, Zagreb (HR); Barbara Mohar, Grosuplje (SI); Damjan Sterk, Ljubljana (SI); Michel Stephan, Vanves (FR)

(73) Assignee: Pliva-Istrazivanje I Razvoj d.o.o. (HR)

( * ) Notice: Subject to any disclaimer, the term of this patent is extended or adjusted under 35 U.S.C. 154(b) by 713 days.

(21) Appl. No.: 11/658,038

(22) PCT Filed: Jul. 21, 2005

(86) PCT No.: PCT/HR2005/000040
§ 371 (c)(1),
(2), (4) Date: Mar. 14, 2007

(87) PCT Pub. No.: WO2006/008562
PCT Pub. Date: Jan. 26, 2006

(65) Prior Publication Data
US 2008/0009629 A1    Jan. 10, 2008

Related U.S. Application Data

(60) Provisional application No. 60/590,608, filed on Jul. 23, 2004.

(51) Int. Cl.
*C07D 215/46* (2006.01)
*C07D 401/00* (2006.01)

(52) U.S. Cl. .............. 546/162; 546/167; 546/171; 546/172; 546/174; 546/175; 546/176

(58) Field of Classification Search .......... 546/162, 546/167, 171, 172, 174, 175, 176
See application file for complete search history.

(56) References Cited

U.S. PATENT DOCUMENTS 6,184,381 B1   2/2001   Ikariya et al.

FOREIGN PATENT DOCUMENTS

EP    0 480 717 A    4/1992

OTHER PUBLICATIONS

Akio Fujii et al., "Ruthenium(II)-Catalyzed Asymmetric Transfer Hydrogenation of Ketones Using a Formic Acid-Trithylamine Mixture", J. Am. Chem. Soc. vol. 118, pp. 2521-2522, 1996.

Damjan Sterk et al., "New Chiral N-(N,N-dialkylamino)sulfamoyl-1,2-diamine ligands for highly enantioselective transfer hydrogenation of ketones", Tetrahedron: Asymmetry, vol. 13, pp. 2605-2608, 2002.

*Primary Examiner*—Janet L. Andres
*Assistant Examiner*—Raymond Covington
(74) *Attorney, Agent, or Firm*—Foley & Lardner LLP

(57) ABSTRACT

The present disclosure relates to an improved process for the preparation of enantiomerically enriched alcohols of Formula (I),

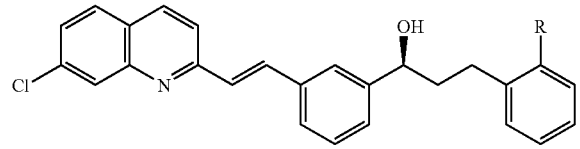

from the corresponding ketone of Formula (II),

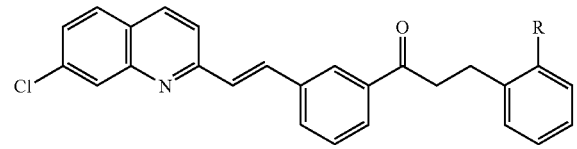

by asymmetric transfer hydrogenation, using a hydrogen donor, catalyzed by a ruthenium or rhodium complex of an optically active N-sulfamoyl-1,2-diamine. R is as defined herein.

21 Claims, No Drawings

FORM OF A BENZENESULFONAMIDE DERIVATIVE

The present disclosure is directed to an improved process for the preparation of enantiomerically enriched alcohols of Formula (I). The process involves asymmetric transfer hydrogenation of the corresponding ketone of Formula (II). R is as defined below.

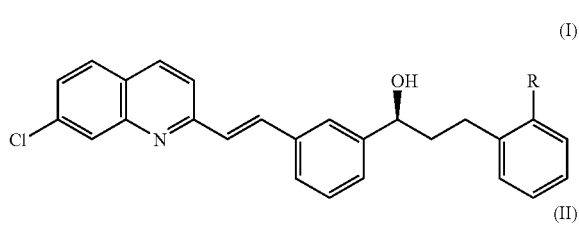

(I)

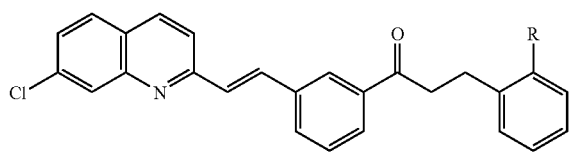

(II)

Methyl [S-(E)]-2-[3-[3-[2-(7-chloro-2-quinolinyl)ethenyl]phenyl]-3-hydroxypropyl]benzoate (1) is a key intermediate in the synthesis of montelukast sodium ([R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropanacetic acid monosodium salt).

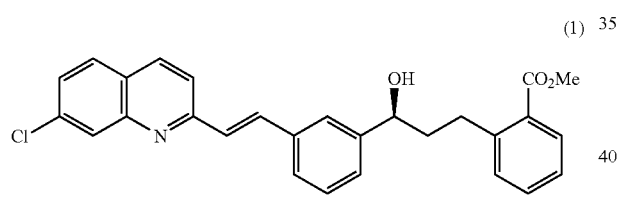

(1)

Montelukast sodium is a leukotriene antagonist, which is effective in the treatment of asthma and associated diseases.

European Patent No. EP 480,717 discloses a process for the preparation of (1) by the borane catalyzed asymmetric reduction of (2) using either an oxazaborolidine complex (3) or (−)-B-chlorodiisopinocampheylborane "(−)-DIP chloride" (4) as the catalyst.

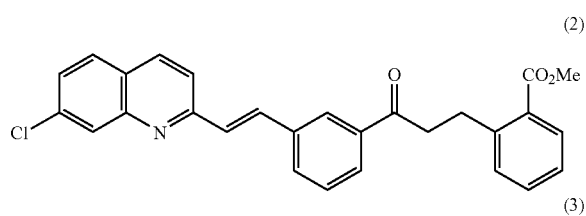

(2)

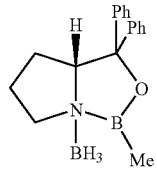

(3)

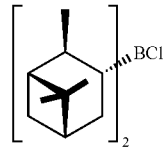

(4)

The synthetic routes disclosed in EP 480,717 have several drawbacks. For example, when using the oxazaborolidine complex (3), the partially over-reduced product (5) is formed in amounts of up to 10%. In order to suppress the formation of (5), a high catalyst loading (up to 55%) is required, thereby rendering this approach unsuitable for commercial use.

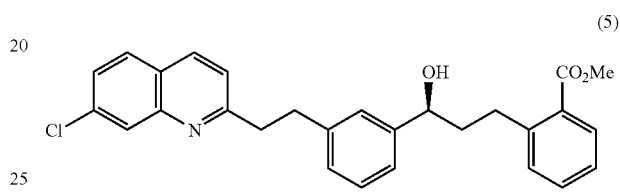

(5)

When (−)-DIP chloride (4) is used in this process, high enantioselectivity and total conversion can only be obtained when at least 1.8 equivalents of this air sensitive and relatively expensive reagent (4) are used, and the reaction is conducted at low temperature (−20° C.).

U.S. Pat. No. 6,184,381 describes a process for the preparation of (1) involving the asymmetric transfer hydrogenation of (2) using chiral ruthenium diamine sulfonyl complexes of the general formula (6):

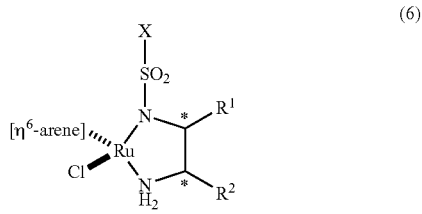

(6)

wherein X is $CH_3$, $CF_3$, p-$CH_3C_6H_4$—, 2,4,6-$(CH_3)_3$ $C_6H_2$—, 1-naphthyl, or campheyl, the $\eta^6$-arene is benzene, p-cymene, mesitylene or hexamethylbenzene, and $R^1$ and $R^2$ are phenyl.

Such catalysts were prepared from [$RuCl_2(\eta^6$-arene)$]_2$ and (S,S)— or (R,R)—N—$XSO_2$-1,2-diphenylethylenediamine by heating in 2-propanol at 80° C. for one hour.

Fujii et al., *J. Am. Chem. Soc.*, 1996, 118, 2521-2522, disclose that compound (2) is reduced using the isolated catalyst RuCl[(1R,2R)—N-tosyl-1,2-diphenylethylenediamine]($\eta^6$-mesitylene) in a mixture of formic acid-triethylamine and THF to yield, after 72 hours, the (R)-enantiomer of (1) in 68% yield and 92% enantiomeric excess (ee).

Sterk et al., *Tetrahedron: Asymmetry*, 2002, 13, 2605-2608, disclose the transfer hydrogenation of acetophenone, methylbenzoylformate, ethylbenzoylformate, and 2-carbomethoxy-1-indanone using chiral Ru(II) and Rh(III) complexes of N-(dialkylamino)sulfamoyl-1,2-diamine.

The present invention relates to an improved process for the preparation of enantiomerically enriched alcohols of Formula (I) from the corresponding ketone (II).

In accordance with the present invention, an improved process for the preparation of enantiomerically enriched alcohols of Formula (I) is provided. The process involves asymmetric transfer hydrogenation of the corresponding ketone (II) using a chiral ruthenium or rhodium catalyst:

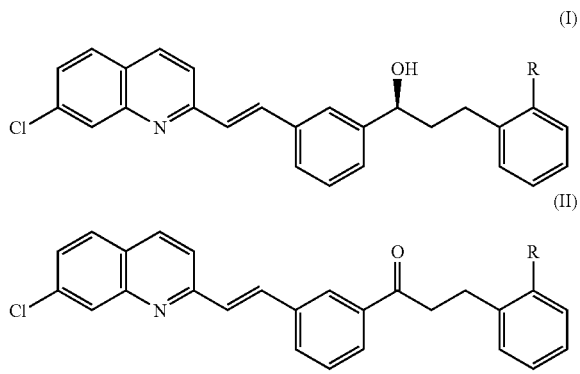

wherein R is selected from hydrogen, halogen, alkyl, cycloalkyl, aryl, heteroaryl, OR', NR'R", SR', S(O)R', SO$_2$R', SO$_3$R', P(O)(OR')(OR"), CO$_2$R', C(O)SR', CONR'R", and CN;

R' and R" are selected from a negative charge, hydrogen, alkyl, cycloalkyl, aryl, or R' and R" may together form a cycloalkyl, aryl or heteroaryl ring that may optionally be substituted by one or more R substituent(s).

The process disclosed herein provides a cost effective route to enantiomerically enriched alcohols that can readily be utilized commercially. The chiral N-sulfamoyl-1,2-diamine-based catalysts used in the present invention can be prepared in situ, are efficient and stable, and do not require the use of special techniques necessary for inert gas operation. Furthermore, the processes described herein allow for easy isolation of the final product (I) in high yield and high enantiomeric purity with increased productivity.

Unless defined otherwise, all technical and scientific terms used herein generally have the same meaning as commonly understood by one of ordinary skill in the preparation of enantiomerically enriched alcohols.

The term "about" or "approximately" means within an acceptable error range for the particular value as determined by one of ordinary skill in the art, which will depend in part on how the value is measured or determined, i.e., the limitations of the measurement system. For example, at about can mean within 1 or more than 1 standard deviations, per the practice in the art. Alternatively, "about" can mean a range of up to 20%, desirably up to 10%, more desirably up to 5%, and even more desirably up to 1% of a given value. Where particular values are described in the application and claims, unless otherwise stated the term "about" meaning within an acceptable error range for the particular value should be assumed.

The term "alkyl," by itself or as part of another substituent, means, unless otherwise stated, a straight or branched chain radical, which may be fully saturated, mono- or polyunsaturated and can include di- and multivalent radicals, having the number of carbon atoms designated (e.g., $C_1$-$C_{10}$ means one to ten carbons). Examples of saturated hydrocarbon radicals include, but are not limited to, groups such as methyl, ethyl, n-propyl, iso-propyl, n-butyl, t-butyl, iso-butyl, sec-butyl, n-pentyl, n-hexyl, n-heptyl, and n-octyl.

Cycloalkyl means a saturated or unsaturated cyclic hydrocarbon radical, such as, but not limited to, cyclopropyl, cyclobutyl, cyclopentyl, cyclohexyl, cyclohexenyl, cyclohepta-1,3-dienyl, cyclooctadienyl, (cyclohexyl)methyl, and cyclopropylmethyl.

The terms "halo" or "halogen," by themselves or as part of another substituent, mean, unless otherwise stated, a fluorine, chlorine, bromine, or iodine atom.

The terms "aryl" and "arene" mean, unless otherwise stated, a substituted or unsubstituted polyunsaturated, aromatic, hydrocarbon substituent, which can be a single ring, or multiple rings (preferably from 1 to 3 rings), which are fused together or linked covalently.

The term "heteroaryl" refers to a category of aryl groups (or rings) that contain from one to four heteroatoms selected from N, O, and S, wherein the nitrogen, carbon, and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl "Aryl", "arene" and "heteroaryl", also encompass ring systems in which one or more non-aromatic ring systems are fused, or otherwise bound, to an aryl, arene, or heteroaryl system.

In a preferred embodiment of the present invention, an improved process for the preparation of methyl [S-(E)]-2-[3-[3-[2-(7-chloro-2-quinolinyl)ethenyl]phenyl]-3hydroxypropyl]benzoate (1) by asymmetric transfer hydrogenation of the corresponding ketone (2) is provided.

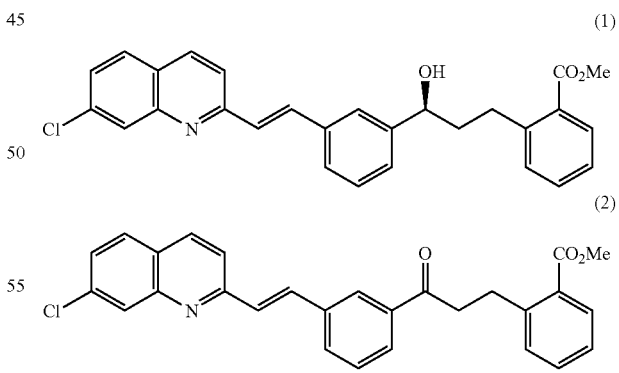

The asymmetric transfer hydrogenation may be conducted using a chiral ruthenium or rhodium catalyst, in the presence of a hydrogen source.

In accordance with the invention, the chiral ruthenium or rhodium catalyst is prepared in situ by reaction of a ruthenium or rhodium catalyst precursor and a chiral N-sulfamoyl-1,2-diamine type ligand, represented by the general Formula (7):

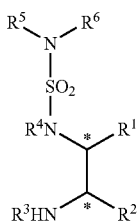

(7)

wherein $R^1$ and $R^2$ independently represent an aryl or cycloalkyl group, or optionally, $R^1$ and $R^2$ may together form a cycloalkyl ring; $R^3$ and $R^4$ independently represent hydrogen or a negative charge; and $R^5$ and $R^6$ independently represent hydrogen, alkyl, cycloalkyl, or aryl, or optionally $R^5$ and $R^6$ together form an optionally substituted nitrogen-containing ring. The symbol * represents an asymmetric carbon atom.

Suitable, but non-limiting, examples of ligands of formula (7) that may be used in the process of the present invention include:

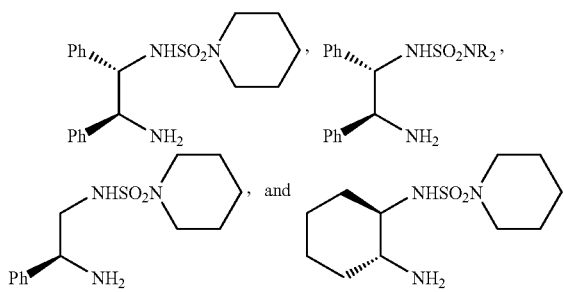

wherein each R is independently selected from alkyl (such as methyl or iso-propyl) and cycloalkyl (such as cyclohexyl), as well as those described in Sterk et al., *Tetrahedron: Asymmetry*, 2002, 13, 2605-2608, which is hereby incorporated by reference in its entirety.

In a more specific embodiment, the ruthenium or rhodium catalyst precursor is an arene-metal halide rhodium or ruthenium complex.

Suitable, but non-limiting examples of ruthenium complexes that may be used in the present invention include $\eta^6$-arene-ruthenium(II) halide dimers of the formula [RuX$_2$($\eta^6$-arene)]$_2$, wherein $\eta^6$-arene represents, but is not limited to, benzene, p-cymene, mesitylene, 1,3,5-triethylbenzene or hexamethylbenzene, and X is a halide, such as chloride, bromide, or iodide. In one example, the ruthenium catalyst precursor is mesitylene ruthenium(II) chloride dimer.

Suitable, but non-limiting examples of rhodium complexes that may be used in the present invention include $\eta^5$-arene-rhodium(III) halide dimers of the formula [RhX$_2$($\eta^5$-arene)]$_2$, wherein $\eta^5$-arene is an optionally substituted cyclopentadienyl ligand, such as, but not limited to, cyclopentadienyl or pentamethylcyclopentadienyl, and X is a halide, such as chloride, bromide or iodide. In one example, the rhodium catalyst precursor is (pentamethylcyclopentadienyl)rhodium (III) chloride dimer.

The catalyst generated by reaction of the ruthenium or rhodium catalyst precursor with the ligand of formula (7) typically has the formula:

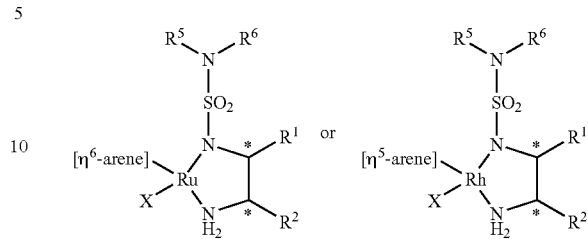

wherein $R^1$, $R^2$, $R^5$, $R^6$, $\eta^6$-arene, and $\eta^5$-arene are as defined above.

The ruthenium catalyst may be used at a concentration of about 0.1 to about 10 mol %, desirably at a concentration of about 0.1 to about 2.5 mol %, and most desirably at a concentration of about 0.5 to about 1.0 mol %.

The rhodium catalyst may be used at a concentration of about 0.5 to about 10 mol %, desirably at a concentration of about 0.5 to about 2.5 mol %, and most desirably at a concentration of about 0.5 to about 1.5 mol %.

The asymmetric transfer hydrogenation is typically carried out in the presence of a hydrogen source. Suitable, but not limiting, hydrogen sources include those-based on HCO$_2$H, such as, HCO$_2$H-Et$_3$N, HCO$_2$H—$^i$Pr$_2$NEt, HCO$_2$H-metal bicarbonate and HCO$_2$H-metal carbonate. Suitable metal carbonates and bicarbonates include, but are not limited to, carbonates and bicarbonates of metals of Group I (such as Na, K, and Cs) and Group II (such as Mg, and Ca), Suitable, non-limiting, examples include Cs$_2$CO$_3$, K$_2$CO$_3$, Na$_2$CO$_3$, Li$_2$CO$_3$, MgCO$_3$ and CaCO$_3$. In one example, the hydrogen source is an HCO$_2$H-Et$_3$N azeotropic mixture.

Suitable solvents for use in the process of the present invention include, but are not limited to, highly polar solvents, such as, N,N-dimethyl formamide (DMF), N,N-dimethylacetamide (DMA), 1-methyl-2-pyrrolidinone (NMP), 1,1,3,3-tetramethylurea (TMU), 1,3-dimethyl-2-imidazolidinone (DMEU), and N,N'-dimethylpropyleneurea (DMPU), and mixtures thereof. Preferred solvents include DMF, DMA, NMP, and mixtures thereof.

The asymmetric transfer hydrogenation may be conducted at reaction temperatures of between about 15° C. and about 70° C., preferably at temperatures of between about 30° C. to about 50° C. Typical reaction times are between about 10 and about 50 hours.

The molar ratio of the ruthenium or rhodium catalyst to the ketone of Formula (II) may be between about 1:50 to about 1:1000, preferably between about 1:70 to about 1:300.

The compound of Formula (I) is typically obtained in greater than about 90% enantiomeric excess, and most typically in greater than about 95% enantiomeric excess.

There is also provided by the present invention a process of preparing montelukast, or a pharmaceutically acceptable salt thereof, wherein a compound of formula (I) is converted to montelukast, or a pharmaceutically acceptable salt thereof, and wherein a compound of formula (I) is prepared from a compound of formula (II) by a process substantially as hereinbefore described. Conversion of a compound of formula (I) to montelukast, or a pharmaceutically acceptable salt thereof, can be carried out by synthetic techniques known in the art.

The following examples illustrates the process of the present disclosure, but should not be construed as limiting the scope of this invention.

EXAMPLE 1

Methyl [S-(E)]-2-[3-[3-[2-(7-chloro-2-quinolinyl)ethenyl]phenyl]-3-hydroxypropyl]benzoate (1)

(a) A red-orange solution of catalyst complex was prepared by reaction of [RuCl$_2$(mesitylene)]$_2$ (31.5 mg, 0.11 mmol Ru) and (1S,2S)-(piperidyl-N-sulfamoyl)-1,2-diphenylethylenediamine (40.2 mg, 0.11 mmol) in DMF (5 ml) by heating at 80° C. for 30 minutes. This solution was then added to a suspension of (2) (5.02 g, 11.0 mmol) in DMF at room temperature. HCO$_2$H-Et$_3$N (5:2, 5.0 mL, 50 mmol) was then added. The reaction mixture was well stirred at 40° C. for 20 hours and then partitioned between CH$_2$Cl$_2$ (50 ml) and water (100 ml). The organic layer was further washed with water (2×100 mL), brine (100 ml), dried over MgSO$_4$ and concentrated. To the residual oil, $^i$PrOAc (40 mL) and water (0.75 ml) were added with stirring. After 15 minutes, heptane (10 ml) was added and the mixture stirred for an additional 15 min. The precipitated product was filtered, washed with heptane/$^i$PrOAc (3×25 ml), heptane (30 ml) and then dried in vacuo to give a light beige powder. Product (1) was in the form of monohydrate; 75% yield (3.88 g), 99.5% ee, purity >98% by HPLC.

(b) Example 1(a) was repeated, except that HCO$_2$H—$^i$Pr$_2$NEt (5:2, 50 mmol) was used instead of HCO$_2$H-Et$_3$N.

EXAMPLE 2

Methyl [S-(E)]-2-[3-[3-[2-(7-chloro-2-quinolinyl)ethenyl]phenyl]-3-hydroxypropyl]benzoate (1)

[RuCl$_2$(mesitylene)]$_2$ (31.5 mg, 0.11 mmol Ru), (1S,2S)-piperidyl-N-sulfamoyl-1,2-diphenylethylenediamine (40.2 mg, 0.11 mmol) and DMF (25 ml) were placed in a flask equipped with magnetic stirring. The mixture was heated at 80° C. for 30 min. The orange-red solution was cooled to room temperature and (2) (5.02 g, 11.0 mmol) and HCO$_2$H—Cs$_2$CO$_3$ (50:1, 50 mmol) were added. The reaction mixture was stirred at 40° C. for 24 h and then partitioned between CH$_2$Cl$_2$ (50 ml) and water (100 ml). The organic layer was washed with water (2×100 ml), brine (100 ml) and dried over MgSO$_4$. The concentrated residue was analyzed by $^1$H NMR spectroscopy, using 20 mol % 1,3,5-trimethoxybenzene as an internal standard. The crude product contained starting ketone (2) (21%), product (1) (77%) and side product (5) (2%). For the determination of enantiomeric excess, product (1) was purified by chromatography on silica gel (eluent CH$_2$Cl$_2$/EtOAc 98:2). The product had 95% ee.

EXAMPLE 3

Methyl [S-(E)]-2-[3-[3-[2-(7-chloro-2-quinolinyl)ethenyl]phenyl]-3-hydroxypropyl]benzoate (1)

[RhCl$_2$CP*]$_2$ (1.5 mg), (1S,2S)-piperidyl-N-sulfamoyl-1,2-diphenylethylenediamine (2.2 mg) and DMF (1 ml) were placed in a flask equipped with a magnetic stir-bar. The mixture was heated at 80° C. for 30 min. The brown solution was cooled to room temperature and (2) (250 mg) and HCO$_2$H—Cs$_2$CO$_3$ (250 μL) were added. The reaction mixture was stirred at 40° C. for 24 h and then partitioned between CH$_2$Cl$_2$ (5 ml) and water (5 ml). The organic layer was washed with water (5 ml), dried over MgSO$_4$, and concentrated, affording a mixture of starting ketone (2) (25%) and product (1) (10%, 49% ee) along with side product (5) (10%) and ethylene-bridge reduced compound (2) (55%).

The present invention is not limited in scope by the specific embodiments described herein. Various modifications of the invention in addition to those described herein will become apparent to those skilled in the art from the foregoing description. Such modifications are intended to fall within the scope of the appended claims.

The invention claimed is:

1. A process for the preparation of a compound of Formula (I)

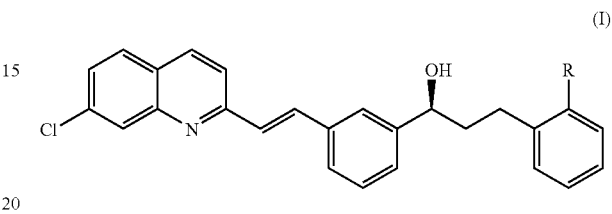

wherein R is selected from hydrogen, halogen, alkyl, cycloalkyl, aryl, heteroaryl, OR', SR', S(O)R', SO$_2$R', SO$_3$R', CO$_2$R', C(O)SR', and CN; and R' is selected from a negative charge, hydrogen, alkyl, cycloalkyl, or aryl, the process comprising (a) contacting, in an organic solvent, a compound having the formula [RuX$_2$(η$^6$-arene)]$_2$ wherein X is a halide; and η$^6$-arene is chosen from benzene, p-cymene, mesitylene, 1,3,5-triethylbenzene and hexamethylbenzene; with a compound of formula (7):

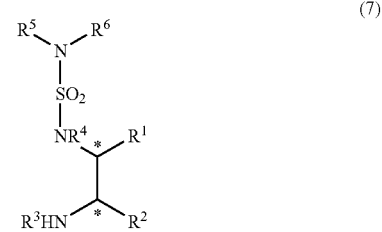

wherein R$^1$ and R$^2$ independently represent an aryl or cycloalkyl group, or optionally, R$^1$ and R$^2$ may together form a cycloalkyl ring;

R$^3$ and R$^4$ independently represent hydrogen or a negative charge;

R$^5$ and R$^6$ independently represent hydrogen, alkyl, cycloalkyl, or aryl, or optionally R$^5$ and R$_6$ together form an optionally substituted nitrogen-containing ring; and (b) contacting the product of step (a) with a compound of Formula (II) in the presence of a hydrogen source:

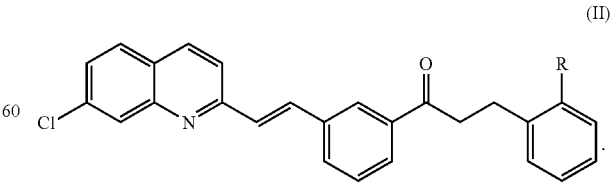

2. The process of claim 1, wherein R is CO$_2$Me.

3. The process of claim 1, wherein the hydrogen source is based on HCO$_2$H.

4. The process of claim 1, wherein the solvent is chosen from NMP, DMA, DMF, TMU, DMEU, DMPU and mixtures thereof.

5. The process of claim 1, wherein the reaction temperature is between about 15° C. and about 70° C.

6. The process of claim 1, where step (b) is conducted for a period of time of between about 10 and about 50 hours.

7. The process of claim 1, wherein the molar ratio of the product of step (a) to the compound of Formula (II) is between about 1:50 to about 1:1000.

8. The process of claim 1, wherein the compound of formula (7) is chosen from:

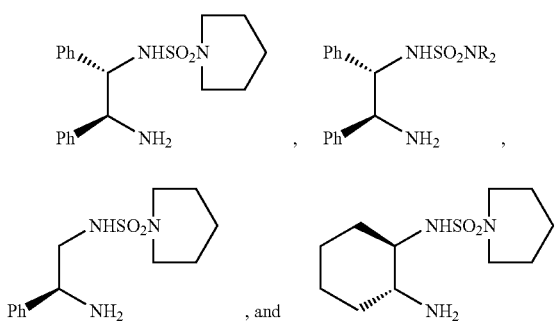

wherein each R is independently selected from alkyl and cycloalkyl.

9. The process of claim 1, wherein the compound of Formula (I) is obtained in greater than about 90% enantiomeric excess.

10. The process of claim 1, wherein the compound of Formula (I) is obtained in greater than about 95% enantiomeric excess.

11. A process for the preparation of a compound of Formula (I)

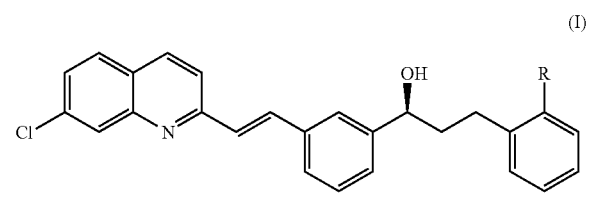

wherein R is selected from hydrogen, halogen, alkyl, cycloalkyl, aryl, heteroaryl, OR', SR', S(O)R', $SO_2R'$, $SO_3R'$, $CO_2R'$, C(O)SR', and CN; and R' selected from a negative charge, hydrogen, alkyl, cycloalkyl, or aryl, the process comprising (a) contacting a compound of Formula (II)

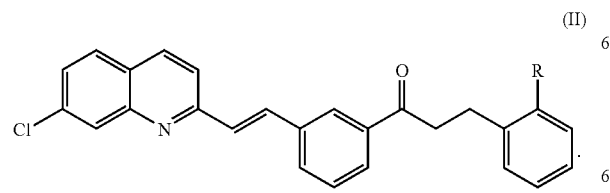

with a compound of Formula:

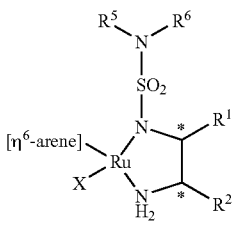

wherein $R^1$ and $R^2$ independently represent an aryl or cycloalkyl group, or optionally, $R^1$ and $R^2$ may together form a cycloalkyl ring;

$R^3$ and $R^4$ independently represent hydrogen or a negative charge;

$R^5$ and $R^6$ independently represent hydrogen, alkyl, cycloalkyl, or aryl, or optionally $R^5$ and $R^6$ may together form an optionally substituted nitrogen-containing ring;

X is a halide; and $\eta^6$-arene is chosen from benzene, p-cymene, mesitylene, 1,3,5-triethylbenzene and hexamethylbenzene;

in the presence of an organic solvent and a hydrogen source.

12. The process of claim 11, wherein R is $CO_2Me$.

13. The process of claim 11, wherein the hydrogen source is based on $HCO_2H$.

14. The process of claim 11, wherein the solvent is chosen from NMP, DMA, DMF, TMU, DMEU, DMPU and mixtures thereof.

15. The process of claim 11, wherein the reaction temperature is between about 15° C. and about 70° C.

16. The process of claim 11, where step (b) is conducted for a period of time of between about 10 and about 50 hours.

17. The process of claim 11, wherein the molar ratio of the product of step (a) to the compound of Formula (II) is between about 1:50 to about 1:1000.

18. The process of claim 11, wherein the compound of Formula (7) is chosen from:

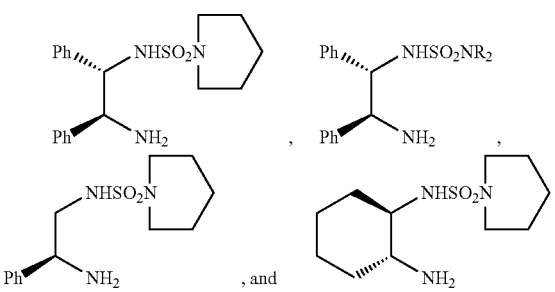

wherein each R is independently selected from alkyl and cycloalkyl.

19. The process of claim 11, wherein the compound of Formula (I) is obtained in more than about 90% enantiomeric excess.

20. The process of claim 11, wherein the compound of Formula (I) is obtained in more than about 95% enantiomeric excess.

21. A process according to claim 1; further comprising converting the compound of Formula I to montelukast, or a pharmaceutically acceptable salt thereof.

* * * * *